US009207466B2

(12) United States Patent
Wildsmith et al.

(10) Patent No.: US 9,207,466 B2
(45) Date of Patent: Dec. 8, 2015

(54) DETERMINING LENS ALIGNMENT ON AN EYE USING OPTICAL WAVEFRONTS

(71) Applicant: Johnson & Johnson Vision Care, Inc., Jacksonville, FL (US)

(72) Inventors: Christopher Wildsmith, Jacksonville, FL (US); Xin Wei, I, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 15 days.

(21) Appl. No.: 14/090,690

(22) Filed: Nov. 26, 2013

(65) Prior Publication Data

US 2015/0146171 A1 May 28, 2015

(51) Int. Cl.
*A61B 3/00* (2006.01)
*G02C 7/04* (2006.01)
*A61B 3/10* (2006.01)
*G06F 17/10* (2006.01)
*G02C 7/02* (2006.01)

(52) U.S. Cl.
CPC ............... *G02C 7/04* (2013.01); *A61B 3/1015* (2013.01); *G02C 7/028* (2013.01); *G02C 7/048* (2013.01); *G06F 17/10* (2013.01); *G02C 2200/04* (2013.01); *G02C 2200/22* (2013.01)

(58) Field of Classification Search
USPC .................................................. 351/200–246
See application file for complete search history.

(56) References Cited

U.S. PATENT DOCUMENTS

| 6,305,802 | B1 | 10/2001 | Roffman et al. |
| 7,497,573 | B2 | 3/2009 | Warden et al. |
| 8,002,407 | B2 | 8/2011 | Warden et al. |
| 2002/0040219 | A1* | 4/2002 | Nakamura et al. ............... 606/5 |
| 2010/0302509 | A1* | 12/2010 | Steinmuller ................... 351/212 |
| 2011/0025979 | A1 | 2/2011 | Chehab et al. |
| 2012/0176581 | A1 | 7/2012 | Bradley et al. |

FOREIGN PATENT DOCUMENTS

| EP | 1902672 A1 | 3/2008 |
| EP | 2560040 A1 | 2/2013 |
| WO | WO 2004099858 A1 | 11/2004 |

OTHER PUBLICATIONS

PCT International Search Report: PCT/US2814/866681 Date of Mailing Feb. 20, 2015.

* cited by examiner

*Primary Examiner* — Mohammed Hasan

(57) ABSTRACT

An apparatus and method for selecting a lens that accounts for Decentration and/or Rotation Errors. The method includes obtaining results of a first wavefront exam on a patient, including a wavefront map and Zernike polynomials, selecting a first lens that improves vision, obtaining the results of a second wavefront exam including a wavefront map and Zernike polynomials, calculating the Decentration and/or Rotation Errors of the selected lens by calculating a difference between the Zernike polynomails, and selecting a second lens that better corrects accounts for the calculated Decentration and/or Rotation Errors.

23 Claims, 4 Drawing Sheets

201   202

203   204

205   206

207   208

DETERMINING LENS ALIGNMENT ON AN EYE USING OPTICAL WAVEFRONTS

FIELD OF USE

The present invention relates generally to field of contact lenses, and more specifically to a system and method for determining rotation error and Decentration Error that occur when a patient wears a given contact lens. This information can be used to select or design a more optimal lens for that patient.

BACKGROUND OF THE INVENTION

It is well known that various eye imaging and analysis technology, such as wavefront imaging, can be used to design and/or select a lens design for a given patient, whether for contacts or glasses. For contact lenses that are worn directly on the eye, it is also known that the physiology of the patient's eye itself, of the patient's eyelid, and the interaction between the two can affects the actual positioning of the lens upon the eye. Often, these factors result in the selected lens orienting itself upon the eye in a less than optimal manner, such as laterally offset from the intended position or at an angular orientation relative to what was intended. This results in less than optimal vision through that lens since the lens is not positioned as designed.

In current practice, an eye care practitioner may attempt to correct these errors by viewing the selected contact lens on the patient's eye, often with the assistance of fiducial, or orientation marks scribed, printed, or otherwise produced upon the lens, and using experience and judgment in viewing the error in position to select another lens that when placed on the eye would better account for the position errors. Typically, another standard or stock lens is then selected for the patient and the process repeated until the eye care practitioner is satisfied with the performance of chosen lens. As this is a manual process dependent on the eye care practitioner's visualization and judgment, the next selected lens may not be optimal for the patient. Further, lenses are often produced without such fiducial marks, rendering it much more difficult and subject to error in the selection process.

The present invention provides a system and method to more precisely measure positional errors of a contact lens on a patient's eye, providing the ability to select or design a subsequent lens for that patient that will better account for such errors.

SUMMARY OF THE INVENTION

The present invention provides a method for selecting a lens that accounts for Decentration Error and/or Rotation Error, including the steps of obtaining results of a first wavefront exam performed on the patient's bare eye, the results including a first wavefront map and a first set of Zernike polynomials, selecting a first contact lens that improves said patient's vision using the results of the first wavefront exam, obtaining results of a second wavefront exam performed on said patient while wearing the selected first contact lens, the second results including a second wavefront map and a second set of Zernike polynomials, calculating Decentration Error or Rotation Error of the selected first lens by calculating a difference between the first and second sets of Zernike polynomials, and selecting a second lens that better accounts for the calculated Decentration Error or Rotation Error of the selected first lens using said calculated difference.

According to one embodiment, the determining step may further include first calculating one of Decentration Error or Rotation Error based upon said calculated difference, generating a third wavefront map and third set of Zernike polynomials that corrects said calculated Decentration Error or Rotation Error, and calculating the other of said Decentration Error or Rotation Error by calculating a difference between the third and second sets of Zernike polynomials, wherein said second selecting step further comprises selecting said second lens that accounts for both said calculated Decentration Error and Rotation Error.

In yet another embodiment, the method may further include, prior to said first calculating step, canceling out any coma terms that were present in said first set of Zernike polynomials.

The method may include wavefront exams that are performed using a wavefront aberrometer.

According to various embodiments, the second selected lens may include a repositioned optic zone as compared to the first selected lens, a corrected cylinder power axis compared to said first selected lens, an alternate base curve compared to said first selected lens, an alternate diameter as compared to said first selected lens, an alternate sag as compared to said first selected lens, an alternate stabilization zone as compared to said first selected lens, or an alternate shape as compared to said first selected lens.

The present invention further an apparatus for identifying a contact lens that improves a patient's vision, including a computer processor, a digital media storage device in communication with the computer processor and storing executable software code which is executable upon demand and operative with the computer processor to receive as input data representing results of a first wavefront exam performed on a patient's bare eye, and results of a second wavefront exam performed on said patient's eye while wearing a first selected contact lens that improves said patient's vision. The input data includes at least a first and second set of Zernike polynomials corresponding to said first and second wavefront exams. The software code can further calculate one of Decentration Error or Rotation Error of the selected lens on said patient's eye by calculating a difference between said first and second set of Zernike polynomials, and identify a second lens suitable for the patient that will substantially correct the calculated Decentration Error or Rotation Error.

The executable software code of the apparatus may further be operative to first calculate Decentration Error of the selected lens on the patient's eye by calculating a difference between the first and second sets of Zernike polynomials, generate a third set of Zernike polynomials that represent the second set of Zernike polynomials as adjusted to offset the calculated Decentration Error, calculate Rotation Error of the selected lens on the patient's eye by calculating a difference between the second and third set of Zernike polynomials, and identify the second selected lens that will substantially correct the calculated Decentration Error and Rotation Error.

In one embodiment, the executable software code may further be operative to, prior to calculating Decentration Error, cancel out any coma terms present in the first set of Zernike polynomials.

In yet another embodiment, the computer processor is in digital communication with a wavefront exam apparatus, and the input data is digitally received from the wavefront exam apparatus. The wavefront exam apparatus may be a wavefront aberrometer.

According to various embodiments, the identified second lens may include a repositioned optic zone as compared to the first selected lens, a corrected cylinder power axis compared to the first selected lens, an alternate base curve compared to the first selected lens, an alternate diameter as compared to the first selected lens, an alternate sag as compared to the first selected lens, an alternate stabilization zone as compared to the first selected lens, or an alternate shape as compared to the first selected lens.

These and other objects, features and advantages of the present invention will be apparent from the following detailed description of illustrative embodiments thereof, which is to be read in connection with the accompanying drawings.

DETAILED DESCRIPTION OF THE INVENTION

Figure 1:
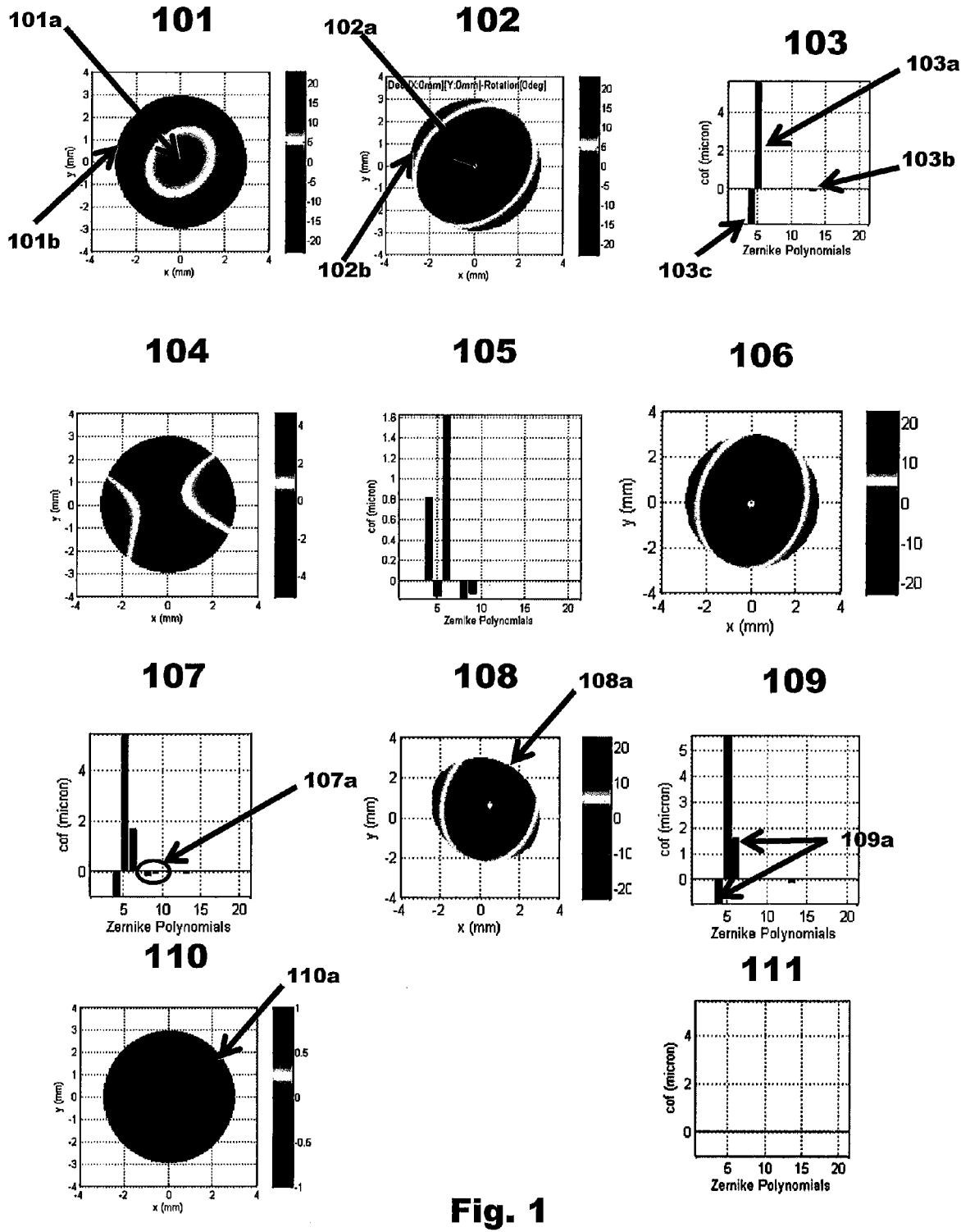
FIG. 1 illustrates an exemplary process of making correctional calculations for positional error of a lens resting upon a patient's eye using wavefront maps and Zernike polynomials.
Figure 2:
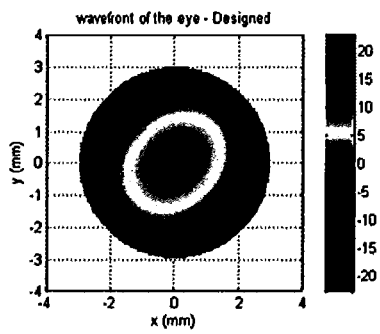
FIG. 2 illustrates a series of exemplary wavefront measurements demonstrating the aberrations resultant from a lens oriented on a patient's eye with Decentration Error and no Rotation Error.
Figure 2:
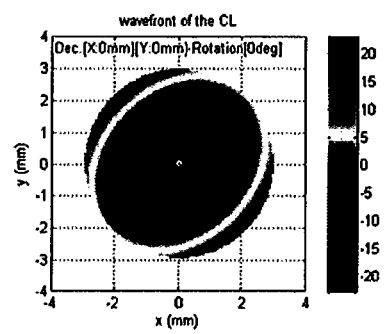
Figure 2:
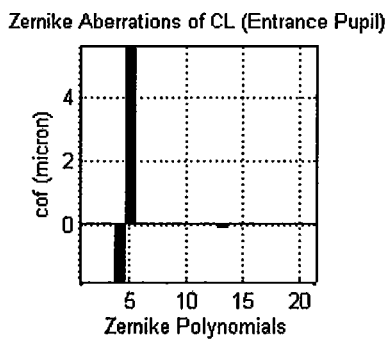
Figure 2:
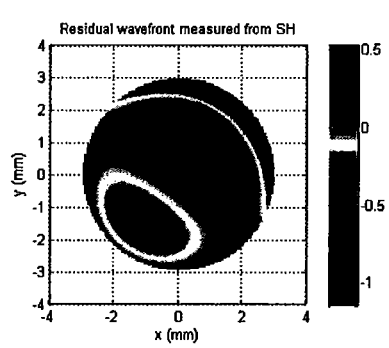
Figure 2:
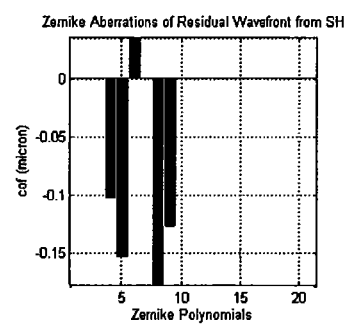
Figure 2:
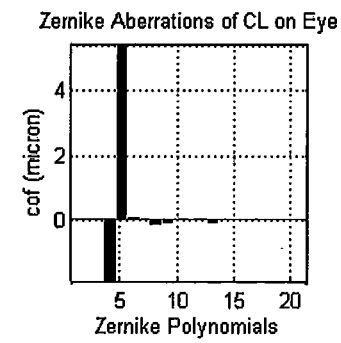
Figure 2:
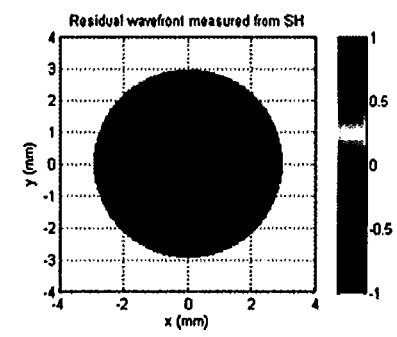
Figure 2:
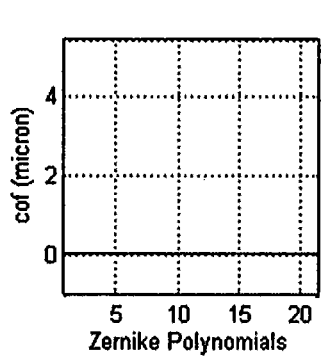
Figure 3:
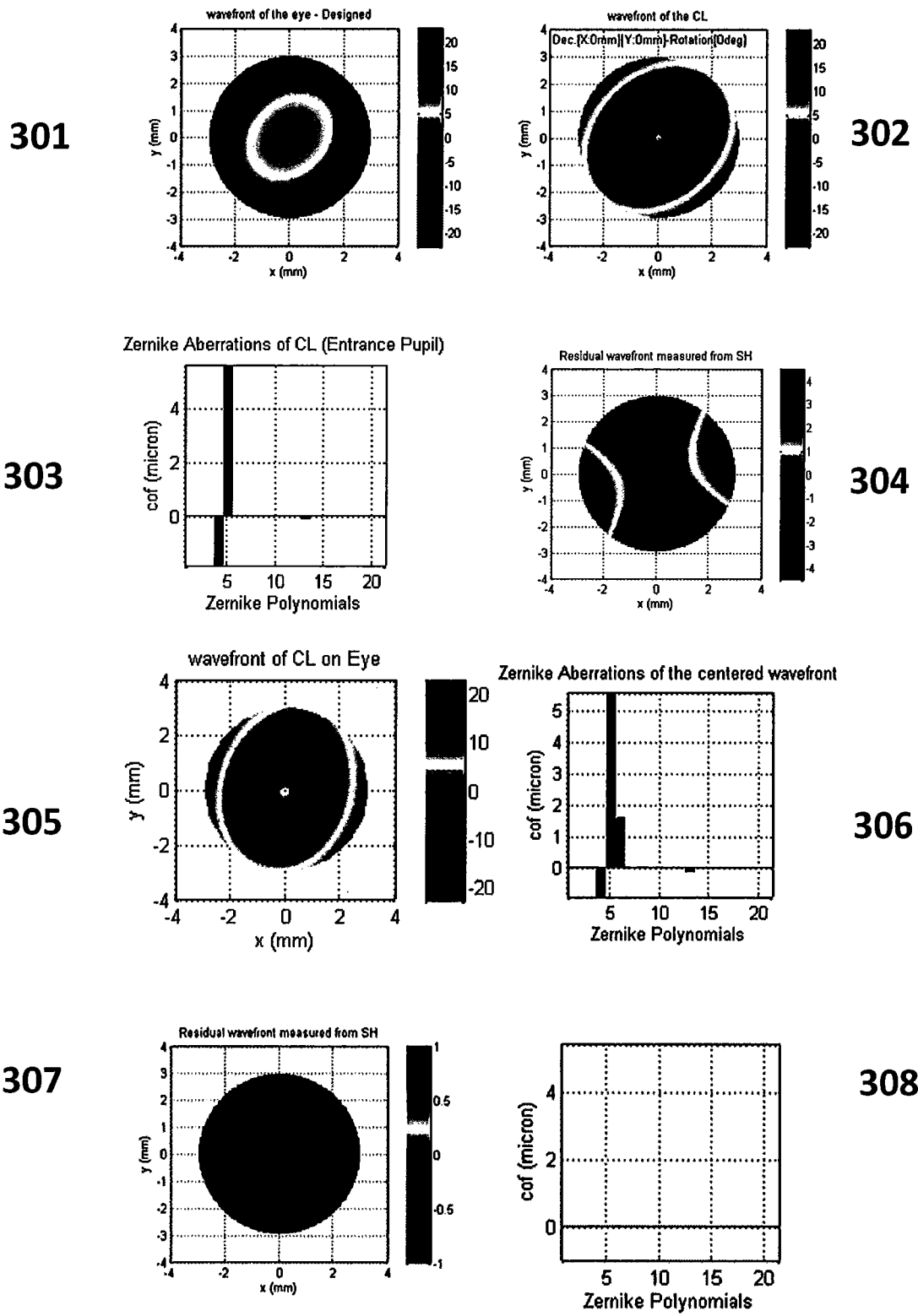
FIG. 3 illustrates a series of exemplary wavefront measurements demonstrating the aberrations resultant from a lens oriented with Rotation Error and no Decentration Error.

The present invention provides a system and method for determining Rotational Error and/or Decentration Error of a contact lens worn when by a given patient. This information may be used to select or design a subsequent custom lens for that patient. In the following sections, detailed descriptions of embodiments and methods will be given. The description of both preferred and alternative embodiments though are exemplary embodiments only, and it is understood that to those skilled in the art that variations, modifications and alterations may be apparent. It is therefore to be understood that the exemplary embodiments do not limit the broadness of the aspects of the underlying invention as defined by the claims.

Glossary

In the description and claims directed to the present invention, various terms may be used for which the following definitions will apply:

"Decentration Error" as used herein, refers to an orientation offset, often descried in terms of (x, y) coordinates, relative to a determined point upon a patient's eye, such as the pupil or iris center, or a limbal edge. For example, a Lens with Decentration Error may orient itself where only a fraction of the Optic Zone sits over pupil region and skewing the corrective power of the Lens.

"Fitting Lens" as used herein refers to a standard, preferably stabilized contact lens that is designed to aid a manufacturer in determining lens position on the eye, or for selecting or designing a contact lens. The fitting lens may have stability and measuring points incorporated in the lens to assist with measuring the rotational position of the lens and the decentration of the lens in relation to the patient's eye.

"Eye Physiology" or "Human Eye Physiology" as referred to herein includes the patient's unique shape of the front portion of the eye (the "anterior chamber") for whom an ophthalmic lens may be generated/customized for best fit. This includes, but is not limited to properties of a patient's eyeball, eye lids, or tear function.

"Lens" as used herein refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses are made from silicone elastomers or hydrogels, which include but are not limited to silicone hydrogels, and fluorohydrogels.

"Lens Design" as used herein, refers to form, function or both of a desired Lens, which if fabricated, may provide optical power correction, acceptable Lens fit (e.g., corneal coverage and movement), acceptable Lens rotation stability, etc. Lens Designs may be represented in either a hydrated or un-hydrated state, in Flat or Curved Space, in 2-dimensional or 3-dimensional space, and by a method including but not limited to, geometric drawings, power profile, shape, features, thicknesses etc. Lens Designs may contain data associated with a regularly or irregularly spaced grid.

"Lens Position Error" as used herein refers to a Lens which orients itself so that a patient suffers diminished fit, comfort, visual acuity, or any other desired aspect of a Lens. This includes, for example, a Lens oriented with Decentration Error or Rotation Error, or both. This may also include a Lens which loses stability as a result of eye movement or a patient's blinking dynamics. Any movement, either static or dynamic, that reduces the effectiveness of any aspect of the Lens may be considered a Lens Position Error.

"Optical Aberration", or "aberration", as used herein, refers to a distortion in an image formed by an optical system. Optical Aberrations may include either one or both of low order aberrations (e.g., sphere power, cylinder power, cylinder axis, etc.) and high order aberrations (e.g., spherical aberration, trefoil, coma, pentafoil, etc.).

"Optimal Lens Position" as used herein, refers to a lens positioned with no Rotation Error or Decentration Error relative to the needed corrective orientation of a Lens on an eye. Additionally, this term may refer to aspects of stability and variation, which may or may not, be the result of eye or eyelid movement.

"Rotation Error" as used herein, refers to a misalignment relative to an angular orientation that meets the needs of a patient's eye. For example, a Lens may orient itself upon a patient's eye at a 30 degree clockwise error, therefor skewing one or multiple of the corrective power axes.

Typically, a patient is given an eye exam as part of the process that an eye care practitioner uses to select a suitable contact lens for that patient. As indicated previously, however, a selected lens may not always behave as anticipated when actually placed on the eye due to the interaction between the lens and the patient's unique Eye Physiology, which may affect lens comfort, fit and/or vision when the lens is on the eye. Measuring and evaluating the positional and rotational parameters of a lens as it sits on a patient's eye, and potentially using that data to determine the appropriate lens that will provide a more Optimal Lens Position is the purpose of the present invention.

A wavefront exam is one test that may be administered on the patient during an eye exam. Generally speaking, a wavefront aberrometer measures how light bends as it is introduced to and returned from the patient's eye. These devices can diagnose both low order vision errors (e.g., nearsightedness, farsightedness and astigmatism) and higher order vision errors (e.g., coma, trefoil and spherical aberration). An exemplary wavefront aberrometer is the OPD-Scan III, which is commercially available from Nidek Co., Ltd. of Japan.

Wavefront aberrometers generate a wavefront map or optical aberration map. Where an aberrometer detects zero optical aberrations, the generated map would be perfectly flat, representing an ideal situation where the bundle of rays remain parallel and undistorted as they pass through the cornea and lens (see e.g., FIG. 110). In reality, imperfections in the eye due to the unique Eye Physiology of any given patient cause distortions of the waves so that the resulting wavefront map represents a non-flat three-dimensional image, with each point on the displayed map representing the difference between zero optical aberrations and the measured optical aberrations. This three-dimensional map is typically displayed with varying colors that correspond to the relative divergence from zero aberrations at any given point. FIG. 101 illustrates a generated wavefront map in grey scale rather than color, although it is readily understood that commercial aberrometers typically provide a colored display.

Different aberrations in the waves passing through an eye have been identified and classified as different vision errors in what is sometimes known as a Zernike pyramid. These identified aberrations can each be represented by a mathematical equation known as a Zernike polynomial. The sum of all the Zernike polynomials describes the total of the optical aberrations or the collective vision error in a given eye. Zernike polynomials are also well known to those skilled in the art of optics and vision science. Wavefront imaging devices may also include, as output, a display identifying Zernike polynomials for the captured image, such as that shown in FIG. 103.

The present invention leverages these technologies in a new and unforeseen manner to provide a system and method that more precisely and consistently determines the Rotation Error and/or Decentration Error of a lens on a patient's eye, which further enables the design selection of a more optimal lens for that patient. Referring now to FIG. 1, a wavefront aberrometer or the like is used to generate a wavefront map of the patient's bare eye, as represented by FIG. 101. As indicated previously, the relative grey scale represents deviations from a perfect eye with, e.g., reference numeral 101a depicting what might be referred to as a "peak" or high point, and reference numeral 101b representing a "valley" or low spot, such that the overall shape if in three dimensions might represent an upside down bowl, elongated in one direction.

Once a wavefront map of a patient's bare eye is generated, those skilled in the art will readily understand how to read such a map and use it to select a contact lens that will better correct the patient's vision. As indicated, however, this selection does not account for any Positional Error that may occur when the lens is actually worn by the patient. FIG. 102 represents a wavefront map for a lens designed or selected to correct for the wavefront error of patient's eye that is revealed by FIG. 101, or alternatively, the wavefront map of a lens, such as a Fitting Lens, that will be placed on the patient's eye for the purpose of evaluating whether the Lens orients itself with a Positional Offset. FIG. 102 represents the wavefront map of the lens itself, independent of a patient's eye. 102a depicts a "valley" and 102b represents a "peak" in a manner somewhat opposite to the error seen in the wavefront map of FIG. 101, with the idea being that the selected lens will "cancel out" or neutralize errors identified in FIG. 101.

FIG. 103 is a graph representing the Zernike polynomial coefficients of the wavefront map of FIG. 102. As alluded to previously, any wavefront can be represented as a weighted linear summation of Zernike polynomials based on these coefficients. The graphical output shown is common in wavefront aberration devices. In this example, the Zernike polynomial coefficients shown in FIG. 103 are representative of the corrective properties of a designed lens, such as that used to generate the wavefront map of FIG. 102. In particular, the Zernike polynomial coefficients at 103a, 103b, and 103c represent the amounts of defocus, spherical aberration, and astigmatism carried in the wavefront map of FIG. 102. The coefficients of all other aberrations terms are zeros in this example.

Next, the selected lens used to generate the wavefront map of FIG. 102 is inserted into the patient's eye. A wavefront exam is then administered with the lens in place, resulting in the wavefront map shown in FIG. 104. If the selected lens optimally corrects the patient's vision, the resulting wavefront map would be perfectly flat, with no peaks and valleys, such as the map shown in FIG. 110. Due to Positional Errors, however, the wavefront map of FIG. 104 shows residual errors. FIG. 105 illustrates the Zernike polynomials for the wavefront map of FIG. 104, which show residual aberrations that exist as a result of Decentration Error and Rotation Error. In this example of FIG. 105, the Zernike polynomials also show error in terms of astigmatism, defocus, and coma, etc.

Next, a wavefront map (FIG. 106) is generated that represents the deviation from or difference between the wavefront map of FIG. 104 (that of the selected lens on the patient's eye) from the wavefront map of FIG. 102 (that of the lens itself). This difference represents the net wavefront error introduced by the decentered and/or rotated lens. FIG. 107 shows the Zernike polynomial coefficients of the wavefront map of FIG. 106, which are different from those shown in 103 due to lens rotation and decentration. In this example, the coma aberration terms 107a are solely due to lens Position Error. A calculation (described further below) may be made to predict the amount of lens decentration from the coefficients of coma aberration terms shown at 107a. If, however, the Zernike polynomials shown in FIG. 103 included coma aberration terms, these coma aberration terms would first need to be neutralized, or subtracted out, so that the remaining Zernike Polynomial coefficients were solely that due to lens decentration.

Once the lens Decentration Errors are obtained, the wavefront error map shown in FIG. 106 can be repositioned. In other words, the map 106 is centered by adjusting the map by an amount and in a corrective direction so that it is positioned as if the lens had not undergone any decentration at all. Another wavefront map represented by FIG. 108 is generated based on the repositioned map, which shows residual wavefront aberrations that remain after the Decentration Errors have been corrected. The portion of the wavefront map at 108a, which is not displayed by a wavefront representation, is due to the fact that then Decentration Errors of the lens have been corrected for by calculation, and an absence of values for a portion of the now centered lens is unavailable because the lens was out of position when the second wavefront exam was administered. FIG. 109 represents the Zernike polynomial coefficients of the wavefront map of FIG. 108. The Zernike polynomial coefficients shown in 109 are different from those shown in 103. As wavefront map 108 has been adjusted for decentration, the difference between the Zernike polynomials of FIGS. 109 and 103 is solely due to lens rotation. Such differences are shown in both astigmatism terms, at 109a. From these terms, a calculation (described further below) may be made to predict the amount of Rotation Error.

Once Decentration Errors and Rotation Error, for the lens as worn by the patient, are obtained, the optic zone of the lens can be adjusted to compensate for any such error. For example, the Decentration Error and Rotation Error data may be converted into (x, y) coordinates. From those coordinates, a new Lens Design may be produced where the optic zone of the new lens is re-positioned by the (x, y) coordinates relative to a peripheral zone, or skirt of the lens. When the newly selected or redesigned lens is centered on the eye, the corrective wavefront of this second lens, as worn by the patient, will now corresponds more closely, if not optimally, to FIG. 102, which is the desired correction for the patient. Summation of the centered, re-designed lens' wavefront and the wavefront errors of the bare eye (FIG. 101) leads to zero aberration as shown in FIG. 110, which is represented by a flat wavefront map. The graph of FIG. 111 illustrates the Zernike coefficients of the zero wavefront aberrations illustrated in FIG. 110. Optically, this means that the residual aberration of the new lens-on-eye system is zero, as the lens fully corrects for the aberration errors of the patient's eye (FIG. 101).

Referring again to FIGS. 101-111, one manner in which the method and calculations described generally above can be implemented will now be described in more detail. From the wavefront map of FIG. 102, the Zernike polynomials shown in FIG. 103 may be denoted as which represents the Zernike polynomial coefficients of the wavefront of the centered designed lens. Next, the actual error of the lens on the eye is calculated by taking the wavefront error of FIG. 104 and finding the difference between that error and the original wavefront error of the eye (FIG. 101). That difference represents the Zernike polynomial coefficients of the net wavefront errors introduced by the actual decentered and rotated lens, which may be represented by $\vec{C}_{CLAcutal\_EP}$.

Since the actual lens on the eye is decentered and rotated, $\vec{C}_{CLAcutal\_EP}$ is different from $\vec{C}_{Design\_EP}$, which corresponds to the Zernike coefficients of the wavefront of lens if it was perfectly centered on the patient's eye. Such difference can be calculated as $\Delta\vec{C}=\vec{C}_{CLAcutal\_EP}-\vec{C}_{Design\_EP}$. The $8^{th}$ and $9^{th}$ Zernike polynomial terms (denoted as '$\Delta C^8$' and '$\Delta C^9$' respectively) in $\Delta\vec{C}$ represent coma terms. As is well known in the art, these terms directly relate with lens vertical and horizontal decentration (denoted as '$\Delta y$' and '$\Delta x$' respectively) and inversely relate with spherical aberration of the centered lens design, which is the $13^{th}$ term (denoted as $C_{Design\_EP}^{13}$) in $\vec{C}_{Design\_EP}$. Therefore, decentration can be readily calculated by a relation as follows:

$$\Delta x = k \frac{\Delta C^9}{C_{Design\_EP}^{13}}, \Delta y = k \frac{\Delta C^8}{C_{Design\_EP}^{13}}$$

(where k is a constant that changes with pupil size)

Once lens Decentration Error is obtained, the wavefront error map can be repositioned, as described above and as shown in FIG. 108. The Zernike coefficients of the wavefront error of FIG. 108 as denoted by $\vec{C}_{adjusted}$, is represented by the graph of FIG. 109. The difference between $\vec{C}_{adjusted}$ and $\vec{C}_{Design\_EP}$ is solely due to lens rotation and can be calculated as follows:

Rotation_angle=

$$\frac{\tan^{-1}(C_{Design\_EP}^{6}/C_{Design\_EP}^{4}) - \tan^{-1}(C_{CL\_adjusted}^{6}/C_{CL\_adjusted}^{4})}{2}$$

wherein: $C_{Design\_EP}^{4}$ and $C_{Design\_EP}^{6}$ represents the $4^{th}$ and $6^{th}$ aberration coefficients in Zernike vector $\vec{C}_{Design\_EP}$; $C_{CL\_adjusted}^{4}$ and $C_{CL\_adjusted}^{6}$ represents the $4^{th}$ and $6^{th}$ aberration coefficients in Zernike vector, $\vec{C}_{CL\_adjusted}$. Once the decentration and rotation of the lens are obtained, the peripheral zone of the lens can be adjusted to compensate for such decentration and rotation as described above. When the adjusted lens is centered on the eye, the residual aberration of lens-on-eye system is zero, as the lens optimally corrects aberration error of the eye.

By way of further example, FIGS. 201-208 and 301-308 and the corresponding description illustrate what could be encountered in a patient that has only Decentration Error (FIGS. 201-208) or only Rotation Error (FIGS. 301-308), but not both, when wearing a selected lens. First, FIGS. 201-208 illustrate a situation where a selected lens, when placed on a patient's eye exhibits only Rotation Error. Similar to that described above with reference to FIGS. 101 and 102, FIG. 201 is a wavefront map of the patient's bare eye; FIG. 202 is a wavefront map of the initially selected lens; and FIG. 203 represents the Zernike polynomials for the wavefront map of FIG. 202. FIG. 204 is a wavefront map of the selected lens as worn by the patient, which is exemplary of a situation where the selected lens orients itself with Decentration Error but no Rotation Error.

FIG. 205 represents the Zernike polynomials of the residual wavefront aberrations which are shown by the wavefront map of FIG. 204. Next, as also described previously, the Zernike polynomials represented in FIGS. 202 and 205 are used to calculate the Decentration Error of the selected lens. The Zernike polynomials resulting from this calculation are shown in FIG. 206, which illustrates the residual aberrations which represent the Decentration Error of the Lens oriented on the eye that must be accounted for when selecting or designing the next lens for the patient.

Assuming that an alternate lens with the desired parameters exists or is custom designed, and when worn by the patient the Lens orients itself similarly to the previous Lens, then the wavefront map of FIG. 207 represents the residual wavefront aberrations of the re-designed lens, resulting in zero residual aberrations as shown in the wavefront map of FIG. 207 and corresponding Zernike polynomials represented in FIG. 208.

FIGS. 301-308 illustrate an example where an initially selected lens, when placed in a patient's eye, exhibits Rotation Error but zero Decentration Errors. FIG. 301 is a wavefront map of the patient's bare eye; FIG. 302 is a wavefront map of an initial lens selected based on the wavefront map of FIG. 301 and designed to correct for the wavefront errors in that wavefront map; and FIG. 303 shows the Zernike polynomials for the needed correction as represented by the wavefront map of FIG. 302. FIG. 304 is a wavefront map taken of the patient's eye while wearing the selected lens. Assuming the selected lens orients itself with Rotation Error and zero Decentration Errors, a wavefront map of the patient wearing that selected lens would reveal aberrations on the wavefront map such as those shown in FIG. 304.

FIG. 305 is a wavefront map representing the calculated residual wavefront aberrations of the rotated lens as derived from the wavefront aberrations of FIGS. 302 and 305. As described above with reference to FIG. 101-111, FIG. 306 represents the Zernike coefficients of FIG. 305, which illustrate residual aberrations that represent the Rotation Error of the Lens oriented on the eye that must be accounted for when selecting or designing the next Lens for the patient to account for the Rotation Error demonstrated by the initial Lens.

Assuming that an alternate Lens with the desired parameters exists or is custom designed, and when worn by the patient the Lens orients itself similarly to the previous Lens, then the wavefront map of FIG. 307 represents the residual wavefront aberrations of the newly selected or re-designed lens, which is zero. FIG. 308 illustrates the Zernike polynomials for the wavefront map of FIG. 307.

Figure 4:
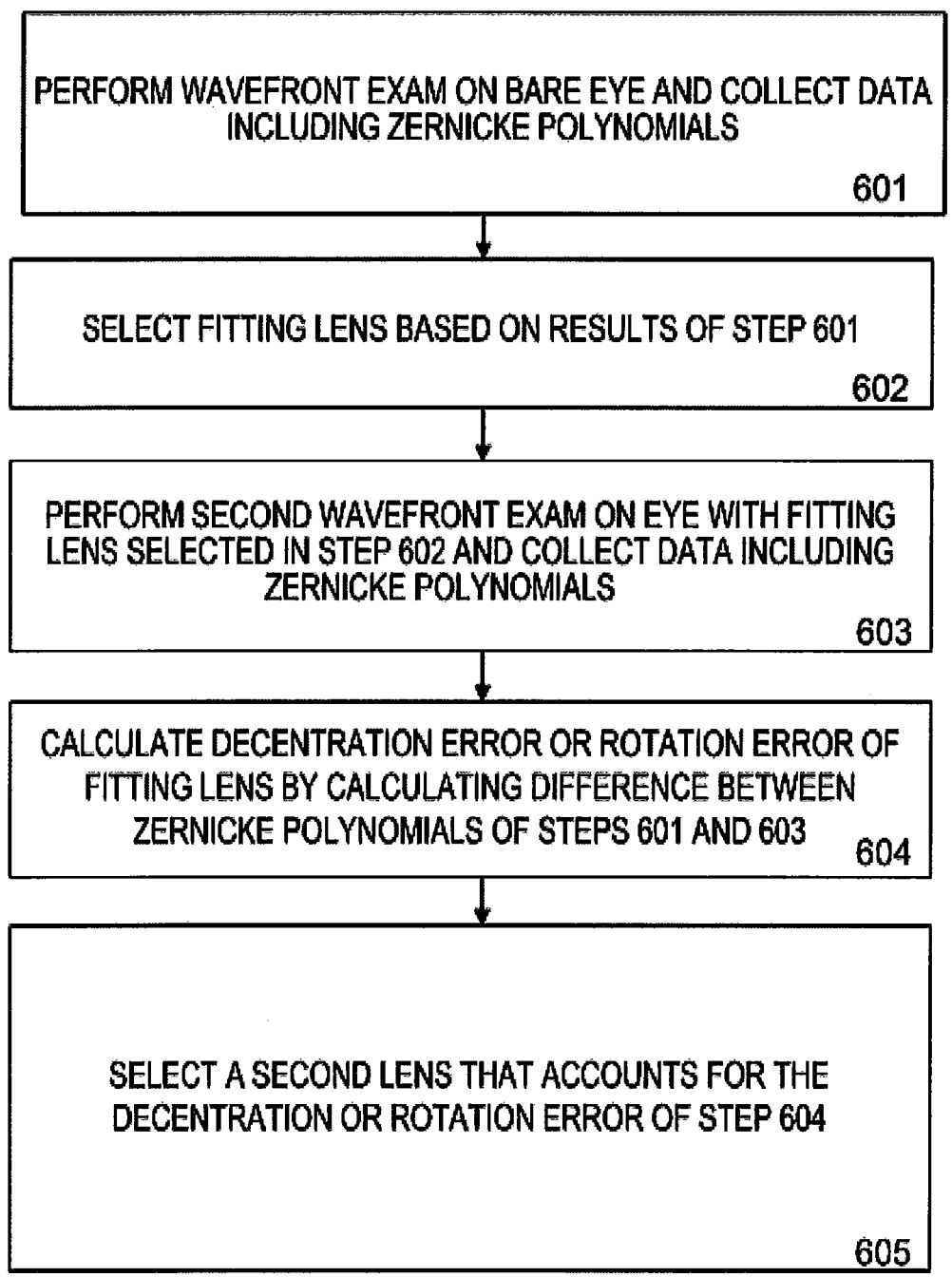
FIG. 4 illustrates in flow chart form an exemplary method of using wavefront data to calculate Positional Offset, and using such information to select or design a more optimal lens for a patient.

Referring now to FIG. 4, a method of extracting wavefront data and calculating Lens Position Error using the wavefront data is shown in flowchart form. Additionally, the flowchart demonstrates the methods of correcting for the Lens Position Error by providing a Lens that accounts for that Lens Position Error.

At 401, a wavefront exam is administered on a patient's bare eye. In an exemplary embodiment, a wavefront exam may be administered with a wavefront aberrometer device, such as the OPD-Scan III noted previously. The wavefront exam provides wavefront refraction data typically in the form of a wavefront map as has also been discussed above. At 402, the wavefront refraction data may then be used to choose an initial lens suitable for the patient. In an exemplary embodiment, the wavefront data, which may or may not be converted into Zernike coefficient space, may be used to select the appropriate standard lens, or alternatively, to select an appropriate Fitting Lens for the patient, and the selected lens is placed onto the patient's eye (403).

At 404, a subsequent wavefront exam is then administered while the patient is wearing the selected Lens, which provides wavefront data such as in the form of a wavefront map, which also may or may not be represented by Zernike coefficients. If the selected lens orients itself with Lens Position Error, this second wavefront exam will provide over-refraction wavefront data. The over-refraction wavefront data may be either in the form of a wavefront map illustrating wavefront aberrations or in the form of Zernike polynomials. Following the extraction of the second set of wavefront refraction data at step 405, the first set of data, from which the original lens was selected, may then be compared to the second set of wavefront refraction data.

Next, at 406, calculations are made using the wavefront data, and in some embodiments, the Zernike polynomial representations of the wavefront data, of the patient's bare eye and of the first selected lens on the patient's eye. The calculations at 406 can determine the Decentration Errors and/or Rotation Error. At 407, based on the errors calculated at 406, a subsequent lens may be selected that provides more optimal vision correction for the patient. This subsequent selected lens may be either a standard lens or a custom lens designed specifically to account for the errors calculated at 406. Additional wavefront exams may be administered, at 408, on the patient wearing the subsequent Lens, and any further lenses necessary, and the same wavefront data calculation method repeated until a Lens results in the Optimal Lens Position available to that patient based on that patient's Eye Physiology.

Once positioning data in terms of Decentration Error and Rotation Error is obtained, a second lens may be either selected or designed. The above examples mainly demonstrate the typical eye care practitioner practice using standard or stock lenses, where there is a finite amount of choices the eye care practitioner has when selected the second or further subsequent lenses. With a custom lens, such as a lens produced through a ContourForm manufacturing process (as is described in detail in U.S. Pat. No. 8,317,505, which is incorporated herein by reference in its entirety), the positioning data provides more options for designing a second or further subsequent lens for the patient.

As mentioned above, one exemplary embodiment is to correct for the positioning error of the entire lens by repositioning only the optic zone relative to the remainder of the lens. This approach allows the lens to retain the same on-eye position, while moving the optic zone to a location on the lens that will provide the patient with the designed vision correction.

In addition to moving the optic zone, additional embodiments exist that involve designing a lens so that it positions differently on the eye than the first lens. One exemplary embodiment is to produce a lens with a different base curve. Standard lens manufacturing practice is to offer a small number of back curve variations in a particular lens product line. A ContourForm manufacturing process may offer a wider selection of base curves or a custom base curve. Therefore, once positioning data has been obtained for a particular lens, an analysis of that data may allow for a design of a lens that incorporates an alternate base curve. The alternate base curve will interact differently with the patient's eye and eye lid, resulting in a different lens position than the first lens. Following the above methods, a series of lenses with alternate base curves may be selected until a minimum lens position error is obtained.

A further exemplary embodiment is designing a second lens with an alternate diameter. A lens edge has the additional condition of also interacting with the patient's eye lids. Therefore, an analysis of the positioning data may allow a lens design with an alternate diameter. This second lens with an alternate diameter may interact differently with the patient's eye and eye lids and therefore result in a different lens position. Following the above methods, a series of lenses designed with alternate diameters may be produced until a minimum lens position error is obtained.

Additionally, a derivative of the interaction between a lens edge in terms of diameter is the interaction between lens and patient's eye in terms of lens shape. Just as a different diameter may interact with a patient's eye and eye lid differently, the same is true of a different lens shape. In an exemplary embodiment, the initial lens shape may be the round shape typical of standard or stock lenses. Positioning data may be analyzed to design a lens with an alternate shape, such as a lens with a wider lower portion and a narrower top portion. The change in lens shape may change the interaction with the patient's eye and eye lid therefore changing the resulting lens positioning. A series of lenses with alternate shapes may be produced until a minimum lens position error is obtained.

A further embodiment may include modifying internal features of the lens. In an exemplary embodiment, a lens may be produced with stabilization zones. Stabilization zones, by design, affect the stability and/or positioning of a lens on an eye. In typical eye care practitioner practice, the standard or stock lenses from which each subsequent lens may be chosen have a finite number of stabilization zone options, if any at all. In a manufacturing process such as ContourForm, it may be possible to produce the stabilization zones to provide a custom fit for the patient. Once the positioning data is obtained and analyzed, a lens design may be produced that modifies one or all of the stabilization zones to result in reduced lens movement on the eye. A series of lens may be produced with alternate stabilization zones until a minimum lens position error is obtained.

Further exemplary embodiments include combined modifications of the above mentioned lens design parameters. For example, lens sag is a function of the dimensions of the lens diameter, base curve and shape. Altering the lens sag may have a similar effect of alternating the base curve, diameter, shape or all three. However, lens sag specifically refers to a distance from the apex to a parallel line with the lens edge, in curved space. A lens may interact with a patient's eye and eye lids differently as a function of sag as opposed to a function of solely base curve, diameter or shape. Consequently, a lens design with alternate sag may also include an alternate diameter and/or shape, but the change in lens position may not be identical to any change in lens position based solely on one of the other parameters of diameter or shape.

Another exemplary embodiment of a combination of the above parameters may include a lens designed with modified stabilization zones and a repositioned optic zone. For example, the second lens, or first few subsequent lenses may be designed with modified stabilization zones. However, the change in lens position due to the modified stabilization zones may not correct for the entire lens positioning error. Once an improved lens position has been accomplished via stabilization zone modification, the optic zone may then be repositioned to correct for the remaining amount of lens position error.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A method for selecting a contact lens that accounts for Decentration Error and/or Rotation Error, comprising the steps of:
    obtaining results of a first wavefront exam performed on the patient's bare eye, the results including a first wavefront map and a first set of Zernike polynomials; selecting a first contact lens that improves said patient's vision using the results of the first wavefront exam;
    obtaining results of a second wavefront exam performed on said patient while wearing the selected first contact lens, the second results including a second wavefront map and a second set of Zernike polynomials;
    calculating Decentration Error or Rotation Error of the selected first lens by calculating a difference between the first and second sets of Zernike polynomials; and
    selecting a second lens that better accounts for the calculated Decentration Error or Rotation Error of the selected first lens using said calculated difference.

2. The method according to claim 1, wherein said determining step further comprises:
    first calculating one of Decentration Error or Rotation Error based upon said calculated difference;
    generating a third wavefront map and third set of Zernike polynomials that corrects said calculated Decentration Error or Rotation Error;
    calculating the other of said Decentration Error or Rotation Error by calculating a difference between the third and second sets of Zernike polynomials; wherein said second selecting step further comprises selecting said second lens that accounts for both said calculated Decentration Error and Rotation Error.

3. The method according to claim 2, further comprising, prior to said first calculating step, canceling out any coma terms that were present in said first set of Zernike polynomials.

4. The method according to claim 1, wherein said wavefront exams are performed using a wavefront aberrometer.

5. The method according to claim 1, wherein said second selected lens includes a repositioned optic zone as compared to the first selected lens.

6. The method according to claim 1, wherein said second selected lens includes corrected cylinder power axis compared to said first selected lens.

7. The method according to claim 1, wherein said second selected lens includes an alternate base curve compared to said first selected lens.

8. The method according to claim 1, wherein said second selected lens includes an alternate diameter as compared to said first selected lens.

9. The method according to claim 1, wherein said second selected lens includes an alternate sag as compared to said first selected lens.

10. The method according to claim 1, wherein said second selected lens includes an alternate stabilization zone as compared to said first selected lens.

11. The method according to claim 1, wherein said second selected lens includes an alternate shape as compared to said first selected lens.

12. An apparatus for identifying a contact lens that improves a patient's vision, comprising:
    a computer processor;
    a non-transitory computer readable storage medium in communication with the computer processor and storing executable software code which is executable upon demand and operative with the computer processor to:
    receive as input data representing results of a first wavefront exam performed on a patient's bare eye, and results of a second wavefront exam performed on said patient's eye while wearing a first selected contact lens that improves said patient's vision, said input data including at least a first and second set of Zernike polynomials corresponding to said first and second wavefront exams;
    calculate one of Decentration Error or Rotation Error of said selected lens on said patient's eye by calculating a difference between said first and second set of Zernike polynomials; and
    identify a second lens suitable for said patient that will substantially correct Said calculated Decentration Error or Rotation Error.

13. The apparatus according to claim 12, wherein said executable software code is further operative to:
    first calculate Decentration Error of said selected lens on said patient's eye by calculating a difference between said first and second sets of Zernike polynomials;
    generate a third set of Zernike polynomials that represent said second set of Zernike polynomials as adjusted to offset said calculated Decentration Error;
    calculate Rotation Error of said selected lens on said patient's eye by calculating a difference between said second and third set of Zernike polynomials; and
    identifying said second selected lens that will substantially correct said calculated Decentration Error and Rotation Error.

14. The apparatus according to claim 13, wherein said executable software code is further operative to, prior to calculating Decentration Error, cancel out any coma terms present in said first set of Zernike polynomials.

15. The apparatus according to claim 12, wherein said computer processor is in digital communication with a wavefront exam apparatus, and wherein said input data is digitally received from said wavefront exam apparatus.

16. The apparatus according to claim 15, wherein said wavefront exam apparatus is a wavefront aberrometer.

17. The apparatus according to claim 12, wherein said identified second lens includes a repositioned optic zone as compared to the first selected lens.

18. The apparatus according to claim 12, wherein said identified second lens includes corrected cylinder power axis compared to said first selected lens.

19. The apparatus according to claim 12, wherein said identified second lens includes an alternate base curve compared to said first selected lens.

20. The apparatus according to claim 12, wherein said identified second lens includes an alternate diameter as compared to said first selected lens.

21. The apparatus according to claim 12, wherein said identified second lens includes an alternate sag as compared to said first selected lens.

22. The apparatus according to claim 12, wherein said identified second lens includes an alternate stabilization zone as compared to said first selected lens.

23. The apparatus according to claim 12, wherein said identified second lens includes an alternate shape as compared to said first selected lens.

\* \* \* \* \*